United States Patent
Tham et al.

(10) Patent No.: US 8,408,203 B2
(45) Date of Patent: Apr. 2, 2013

(54) SYSTEM AND METHODS FOR VENTILATING A PATIENT

(75) Inventors: Robert Tham, Middleton, WI (US); Jaron Matthew Acker, Madison, WI (US)

(73) Assignee: General Electric Company, Schenectady, NY (US)

( * ) Notice: Subject to any disclaimer, the term of this patent is extended or adjusted under 35 U.S.C. 154(b) by 1007 days.

(21) Appl. No.: 12/432,902

(22) Filed: Apr. 30, 2009

(65) Prior Publication Data

US 2010/0275920 A1    Nov. 4, 2010

(51) Int. Cl.
*F16K 31/02* (2006.01)
*A62M 15/00* (2011.01)
*A62M 16/00* (2011.01)

(52) U.S. Cl. ......... 128/204.21; 128/200.14; 128/200.24; 128/204.18; 128/204.23

(58) Field of Classification Search ............. 128/200.14, 128/200.24, 204.18, 204.21, 204.23
See application file for complete search history.

(56) References Cited

U.S. PATENT DOCUMENTS

| | | | |
|---|---|---|---|
| 6,588,422 B1 * | 7/2003 | Berthon-Jones et al. | 128/204.23 |
| 2003/0213491 A1 * | 11/2003 | Berthon-Jones et al. | 128/204.18 |
| 2005/0109340 A1 | 5/2005 | Tehrani | |
| 2007/0101992 A1 | 5/2007 | Soliman et al. | |
| 2008/0185009 A1 | 8/2008 | Choncholas et al. | |
| 2009/0241957 A1 * | 10/2009 | Baker, Jr. | 128/204.23 |
| 2010/0275920 A1 * | 11/2010 | Tham et al. | 128/204.23 |
| 2012/0055476 A1 * | 3/2012 | Choncholas | 128/204.22 |

FOREIGN PATENT DOCUMENTS

WO   2009120639 A2   10/2009

OTHER PUBLICATIONS

European Search Report and Written Opinion, EP10161342, Jul. 19, 2010.

* cited by examiner

*Primary Examiner* — Lynne Anderson
*Assistant Examiner* — Bradley Philips

(57) ABSTRACT

System and methods for ventilating a patient are provided. In one embodiment, the method comprises steps of placing a ventilator in a mode capable of delivering respiratory gas based on at least one fixed parameter and at least one variable parameter, the fixed parameters being tidal volume and peak airway pressure and the variable parameter being PEEP, identifying a first level for the PEEP, configuring the ventilator to deliver the respiratory gas at the peak airway pressure and the PEEP to achieve the tidal volume, monitoring respiratory gas flow over time to measure tidal volume, setting a second level for the PEEP based on the measured tidal volume, automatically adjusting the PEEP to the second level relative to the peak airway pressure and repeating the steps of configuring, monitoring, setting and automatically adjusting to achieve the ventilation.

16 Claims, 3 Drawing Sheets

SYSTEM AND METHODS FOR VENTILATING A PATIENT

FIELD OF INVENTION

The invention generally relates to the field of ventilating human patients and more particularly to an improved method for controlling a ventilator.

BACKGROUND OF THE INVENTION

A medical ventilator delivers gas to a patient's respiratory tract and is often required when the patient is unable to maintain adequate ventilation. Known ventilators typically include a pneumatic system that delivers and extracts gas pressure, flow and volume characteristics to the patient and a control system (typically consisting of knobs, dials and switches) that provides an interface to a treating clinician. Optimal support of the patient's breathing requires adjustment by the clinician of the pressure, flow, and volume of the delivered gas as the condition of the patient changes. Such adjustments, although highly desirable, are difficult to implement with known ventilators as the ventilator demands continuous attention and interaction from the clinician.

On the other hand, recruitment maneuvers require the lungs to reach elevated peak pressures generally about 40 cm H2O. As the lung compliance increases during lung recruitment, it is possible to put large volumes of respiratory as into the lungs, potentially hyperventilating the patient. Excessive washout of $CO_2$ (commonly referred as Hypocapnea) alters blood acidity, which can drastically increase systemic vascular resistance, cardiac arrhythmias, and can lead to severe adverse hemodynamic reactions. Hypocapnea is also associated with bronchoconstrictions, bronchospasms and increased airway resistances.

In order to achieve a more consistent level of $CO_2$ elimination during recruitment, the volume of respiratory gas delivered into the lungs of the patient is to be controlled. This can be achieved by breath-to-breath adjustment of one of the peak inspiratory pressure and the PEEP. In practice, this cannot be achieved manually.

In order to achieve a consistent level of $CO_2$ elimination, one of the prior arts describes a volume controlled ventilation mode, where the inspiratory pressure is adjusted to maintain a set tidal volume.

In another prior art, the clinician manually tries to titrate PEEP, as an alternative to varying the peak inspiratory pressure, to maintain a set tidal volume.

Hence there exists a need to provide a ventilator, which is easy to operate and can also provide increased safety and reliability for the patients.

BRIEF DESCRIPTION OF THE INVENTION

The above-mentioned shortcomings, disadvantages and problems are addressed herein which will be understood by reading and understanding the following specification.

In one embodiment, a method of ventilating a patient is provided. The method comprises steps of placing a ventilator in a mode capable of delivering respiratory gas based on at least one fixed parameter and at least one variable parameter, the fixed parameters being tidal volume and peak airway pressure and the variable parameter being PEEP, identifying a first level for the PEEP, configuring the ventilator to deliver the respiratory gas at the peak airway pressure and the PEEP to achieve the tidal volume, monitoring respiratory gas flow over time to measure tidal volume, setting a second level for the PEEP based on the measured tidal volume, automatically adjusting the PEEP to the second level relative to the peak airway pressure and repeating the steps of configuring, monitoring, setting and automatically adjusting to achieve the ventilation.

In another embodiment, a method of ventilating a lung in a patient is provided. The method comprises steps of determining a first peak airway pressure, selecting a first level for the PEEP, providing respiratory gas to the patient at the first peak airway pressure and the PEEP to deliver a first volume of respiratory gas, varying the peak airway pressure to a second value, monitoring respiratory gas flow over time to measure tidal volume, determining a second level for the PEEP based on the measured tidal volume, automatically adjusting the PEEP to the second level relative to the peak airway pressure and providing the respiratory gas to the patient at the second peak airway pressure and the PEEP to deliver a second volume of the respiratory gas.

In yet another embodiment, a ventilator for respiratory treatment of a patient is provided. The ventilator comprises a gas delivery unit for delivering respiratory gas to the patient based on at least one fixed parameter and at least one variable parameter, the fixed parameters being tidal volume and peak airway pressure and the variable parameter being PEEP and a regulation unit for controlling the gas delivery unit to deliver respiratory gas at a pressure level corresponding to the peak airway pressure, the regulation unit further configured for controlling the gas delivery unit for adjusting the PEEP for each breath to maintain the tidal volume equal to a predetermined value.

In yet another embodiment, a computer readable media comprising computer readable program instructions for ventilating a patient is provided. The computer readable program instructions comprising a routine for placing a ventilator in a mode capable of delivering respiratory gas based on at least one fixed parameter and at least one variable parameter; the fixed parameters being tidal volume and peak airway pressure and the variable parameter being PEEP, a routine for identifying a first level for the PEEP, a routine for configuring the ventilator to deliver the respiratory gas at the peak airway pressure and the PEEP to achieve the tidal volume, a routine for monitoring respiratory gas flow over time to measure tidal volume, a routine for setting a second level for the PEEP based on the measured tidal volume, a routine for automatically adjusting the PEEP to the second level, relative to the peak airway pressure and a routine for repeating the steps of configuring, monitoring, setting and automatically adjusting to achieve the ventilation.

Systems and methods of varying scope are described herein. In addition to the aspects and advantages described in this summary, further aspects and advantages will become apparent by reference to the drawings and with reference to the detailed description that follows.

DETAILED DESCRIPTION OF THE INVENTION

In the following detailed description, reference is made to the accompanying drawings that form a part hereof, and in which is shown by way of illustration specific embodiments, which may be practiced. These embodiments are described in sufficient detail to enable those skilled in the art to practice the embodiments, and it is to be understood that other embodiments may be utilized and that logical, mechanical, electrical and other changes may be made without departing from the scope of the embodiments. The following detailed description is, therefore, not to be taken in a limiting sense.

Figure 1:
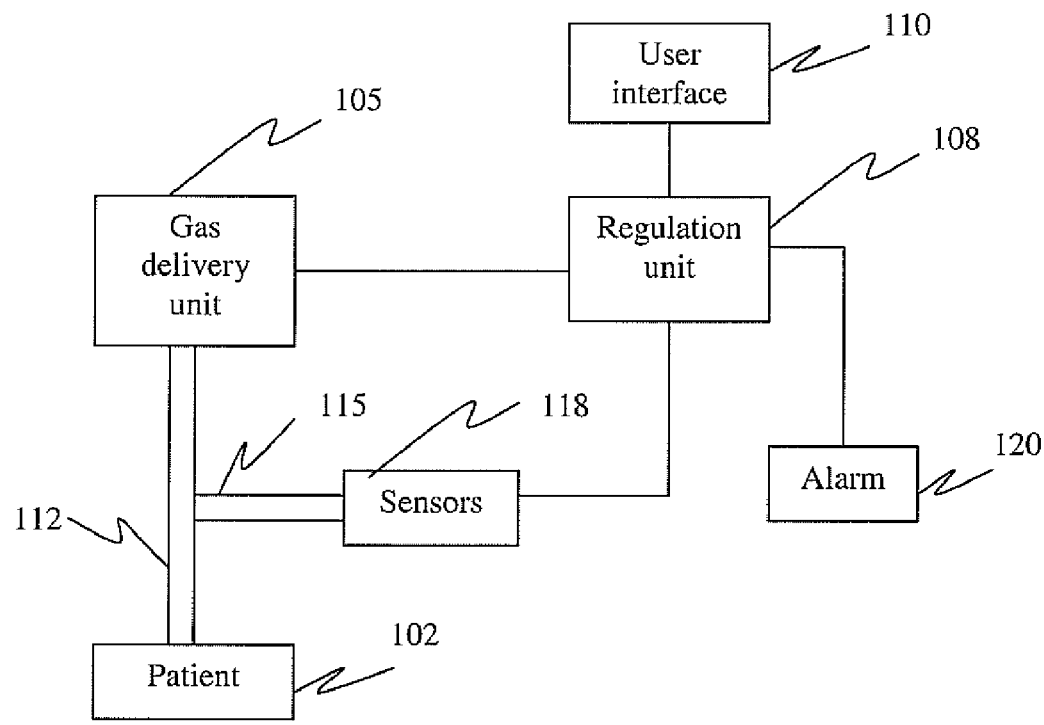
FIG. 1 shows a block diagram of a ventilator, in accordance with an embodiment.

In one embodiment, as shown in FIG. 1, a ventilator 100 for respiratory treatment of a patient 102 is provided. The ventilator 100 includes a gas delivery unit 105 that is in communication with the patient 102 or other living being. The gas delivery unit 105 is configured for delivering respiratory gas to the patient 102 based on at least one fixed parameter and at least one variable parameter.

The fixed parameters may be tidal volume and peak airway pressure and the variable parameter may be PEEP. The peak airway pressure may be peak inspiratory pressure defined by a user operating the ventilator 100. Further, the peak airway pressure can be selected to be about 40 cm $H_2O$ for example. The tidal volume refers to a constant inspired or expired tidal volume. The inspired and expired tidal volume is proportional to patient lung mechanical properties.

The ventilator 100 further includes a regulation unit 108 that is in communication with the gas delivery unit 105. The regulation unit 108 is configured for controlling the gas delivery unit 105 to deliver the respiratory gas at a pressure level corresponding to the peak airway pressure. The regulation unit 108 is further configured for controlling the gas delivery unit 105 for adjusting the PEEP for each breath to maintain the tidal volume equal to a predetermined value.

The regulation unit 108 may further be in communication with a user interface 110. The user interface 110 may be adapted to enable the user to provide the regulation unit 108 with information that, in turn, enables the regulation unit 108 to operate the gas delivery unit 105. The user interface 110 typically includes a graphical user interface 110 as well as a keyboard and/or pointing device to enable the user to select the operating mode of the ventilator 100 and/or to enter or edit patient data and operating parameters such as the pressures, times, flows, and/or volumes associated with one or more ventilation cycles. The user interface 110 also permits display, via a monitor, of measurements, trends or other data in alphanumeric and/or graphical format.

In one embodiment, the user interface 110 is a touch screen used in conjunction with a display. The display is one of a CRT and a flat panel display. More specifically, the display provides a visual indication of the current breath control parameters, alarm and fault conditions, and the current status of the pulmonary system of the patient, including respiratory gas pressure, flow and volume.

In FIG. 1 the ventilator 100 is shown connected to the patient 102 through an inspiration tube 112 and an expiration tube 115. A plurality of sensors 118, such as pressure or flow sensors and oxygen sensors are provided in at least one of the inspiration tube 112 and the expiration tube 115. Those parts of the ventilator 100, which are not of importance for the explanation of the invention, have been omitted from FIG. 1.

The regulation unit 108 of the ventilator 100 includes the capability to process data generated based on inputs from the sensors 118 and determine variety of parameters. The sensors 118 are configured for measuring ventilation parameters including airway flow, airway pressure, airway resistance, makeup of inspiratory gasses, expiratory gasses and/or blood gasses including the partial pressures of oxygen, carbon dioxide in the bloodstream of the patient 102 and the level of oxygen saturation in the blood. Based on pressure and flow measurements, the regulation unit 108 of the ventilator 100 is capable of calculating inspiratory and expiratory gas volumes using the equation Airway Pressure=(Delivered Volume/Lung Compliance)+(Airway Flow. times. Airway Resistance).

By monitoring the pressures being sensed by the pressure sensor and knowing the corresponding volumes of the respiratory gas being delivered by the gas delivery unit 105, the regulation unit 108 may determine the pressure-volume characteristics of the lungs of the patient 102. These characteristics may then be used to fine tune or adjust the control parameters of the ventilator 100.

During the treatment of patient 102 with fragile lungs such as the patient 102 with acute respiratory distressed syndrome or acute lung injury, surgical patient with compromised diaphragmatic or chestwall compliance, or neonate with heterogenous lung compliances secondary to insufficient surfactant, a clinician may want to target a peak pressure and set tidal volume, and have the ventilator 100 adjust PEEP automatically. Alveolar recruitment strategy is another example when it may be desirable to guarantee a fixed user determined distending peak pressure in order to achieve maximum recruitment while maintaining a substantially constant tidal volume during the expiration phase of the recruitment maneuver breaths. For this purpose, the invention describes methods of ventilation, wherein peak lung recruiting pressures are reached while maintaining a constant inspired or expired tidal volume throughout the ventilation process. One of the methods in explained in conjunction with FIG. 2.

Figure 2:
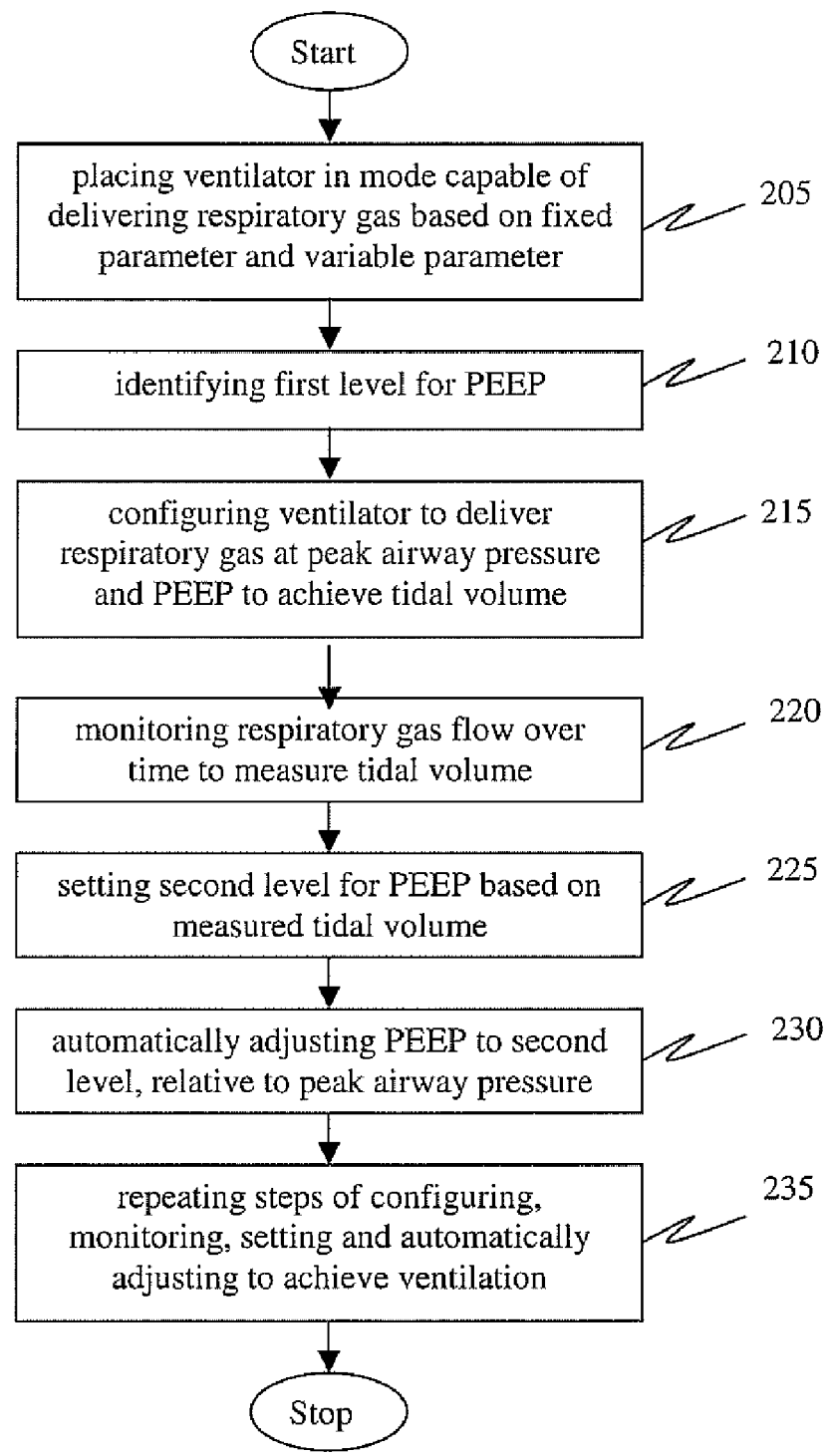
FIG. 2 shows a flow diagram depicting a method of ventilating a patient in accordance with an embodiment.

In one embodiment, as shown in FIG. 2, a method 200 of ventilating the patient 102 is provided. The method 200 comprises steps of placing the ventilator 100 in a mode capable of delivering respiratory gas based on at least one fixed parameter and at least one variable parameter step 205. The fixed parameters may be tidal volume and peak airway pressure and the variable parameter may be PEEP. The fixed parameter may further comprise oxygen content of the respiratory gas, respiratory rate, inspiratory to expiratory ratios and expiration and inspiration time.

The mode of ventilation is selected from the group consisting of pressure control, flow control, volume control and pressure regulated volume control mode of ventilation. Pressure regulated volume control is a ventilator mode where breaths are delivered mandatory to assure preset tidal volumes, with a constant inspiratory pressure continuously adapting to patient's condition. However, in one embodiment, the ventilator 100 may also be configured to operate in a new ventilation mode, where the peak airway pressure is fixed but the PEEP is varied to maintain a fixed or a sequence of targeted tidal volumes.

The method 200 further comprises identifying a first level for the PEEP step 210. The first level for the PEEP is identified based on airway impedance of the patient 102. The airway impedance of the patient 102 is dependent on one or more mechanical properties of the lung, one such mechanical property of the lung being lung compliance. Measuring airway impedance comprises determining airway resistance which is followed by calculating effective airway pressure based upon the measured airway resistance.

Further, the method 200 comprises configuring the ventilator 100 to deliver the respiratory gas at the peak airway pressure and the PEEP to achieve the set tidal volume step 215. The user, for example clinician, enters numerical data for the fixed parameters, relating to the desired level of peak airway pressure or the tidal volume, at the user interface 110. These entered values signal the gas delivery unit 105 to change the amount of PEEP, on a per breath basis, until the pressure in the inspiratory tube equals the value entered by the clinician. Subsequently, PEEP is applied to the patient airway to assist the patient's exhalation through the medical ventilator 100, such that the ventilator 100 delivers a predetermined value of the tidal volume to the patient 102.

The method 200 further comprises steps of monitoring respiratory gas flow over time to measure tidal volume step 220, setting a second level for the PEEP based on the measured tidal volume step 225, automatically adjusting the PEEP to the second level, relative to the peak airway pressure, step 230 and repeating the steps of configuring, monitoring, setting and automatically adjusting to achieve the ventilation step 235.

The first breath delivered to the patient 102 is a volume controlled breath. The measured plateau pressure is used as the pressure level for the next breath. The set tidal volume is achieved by automatic, breath by breath PEEP regulation. The ventilator 100 is configured to adjust the PEEP, based upon the mechanical properties of the lung to the lowest possible level to guarantee the preset tidal volume. When the measured tidal volume increases above the preset, the pressure level decreases in steps, between consecutive breaths until preset tidal volume is delivered.

In another embodiment, the inspired or expired tidal volume can be adjusted based on measured tidal volume, or $CO_2$ elimination which can be determined using ventilation flow rates and $CO_2$ concentration measurements. Such target tidal volume adjustment may help conserve elimination of $CO_2$ despite the shift of large volumes of the respiratory gas into the lungs, which tend to dilute $CO_2$ in the lung.

In one embodiment, the method 200 is executed in a pressure control-volume targeted mode of ventilation, where PEEP is automatically adjusted relative to the peak airway pressure, as determined (or pre-determined) by the recruitment maneuver or the clinician. This allows peak lung recruiting pressures to be reached while maintaining a constant inspired or expired tidal volume throughout the ventilation process. This empowers a clinician who is not as well trained to successfully deliver recruitment maneuvers.

Figure 3:
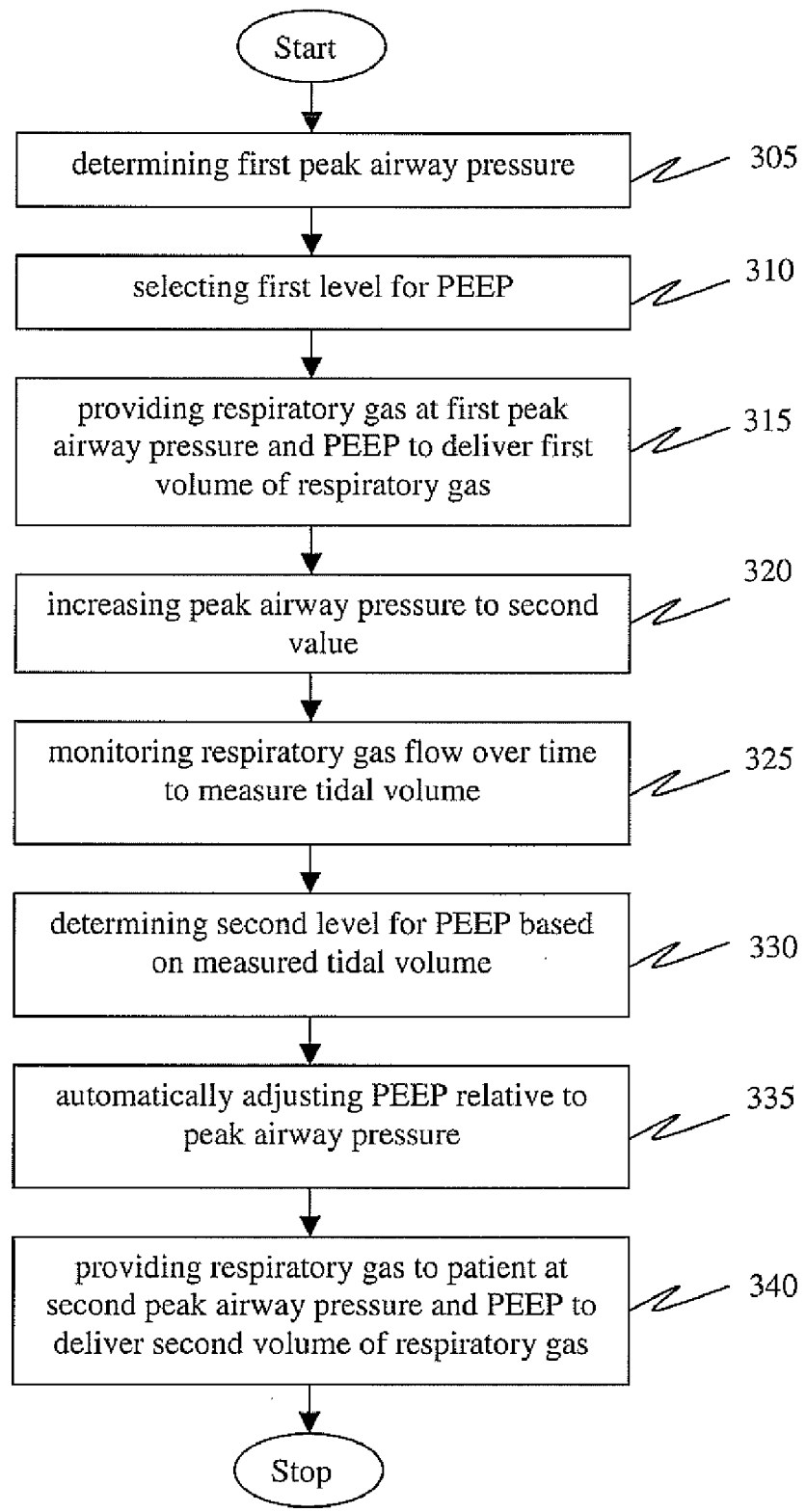
FIG. 3 shows a flow diagram depicting a method of ventilating the patient in accordance with another embodiment.

In another embodiment, as an alternative to maintain a constant inspired and/or expired tidal volume, a sequence of targeted tidal volumes may be observed. In some instances, the tidal volumes may be delivered in a predetermined pressure, flow or volume profile. Accordingly, as shown in FIG. 3, another method 300 of ventilating the patient 102 is provided. The method 300 comprises steps of determining a first peak airway pressure step 305, selecting a first level for the PEEP step 310, providing respiratory gas to the patient 102 at the first peak airway pressure and the PEEP to deliver a first volume of the respiratory gas to the patient 102 step 315, varying the peak airway pressure to a second value step 320, monitoring respiratory gas flow over time to measure tidal volume step 325, determining a second level for the PEEP based on the measured tidal volume step 330, automatically adjusting the PEEP to the second level, relative to the peak airway pressure, step 335 and providing the respiratory gas to the patient 102 at the second peak airway pressure and the PEEP to deliver a second volume of the respiratory gas to the patient step 340.

In method 300, each of the volumes of the respiratory gas being delivered is based upon a corresponding predetermined peak airway pressure. Varying the peak airway pressure comprises increasing or decreasing the peak airway pressure. The PEEP is adjusted breath to breath relative to the peak airway pressure. The adjustment of PEEP can be based of inspiratory volume and change in peak airway pressure and/or expiratory volume and change in peak airway pressure.

During the phase of the recruitment maneuver where peak pressure is increasing stepwise, the PEEP adjustment to achieve the fixed tidal volume, at the peak airway pressure, is based on the respiratory gas volume exhaled during expiration.

Typically, expired tidal volumes exhaled during the expiration phase of ventilation are considered to adjust the PEEP. Failing to do so may result in inappropriate and delayed release of the respiratory gas from the lung as the peak pressures are reduced. For example, during the phase of recruitment maneuver that comprises decreasing the peak airway pressure below the level of adjusted PEEP for the breath preceding a selected breath, the respiratory gas in the patient lungs, subtended by the preceding and higher adjusted PEEP, prior to the decrement of the peak airway pressure, may initiate release of respiratory gas from the lungs during the inspiration. Therefore, during the execution of the recruitment maneuver, when the peak airway pressure is reduced stepwise, the users typically fix the stepwise decrement of the PEEP thereby allowing the peak pressure to be adjusted to obtain the fixed tidal volume. Thus, during the phase of the recruitment maneuver where peak pressure is decreasing stepwise, the PEEP adjustment to achieve the fixed tidal volume, at the peak airway pressure, is based on the respiratory gas volume inhaled during inspiration.

Thus, the method 300 of ventilation allows peak lung recruiting pressures to be reached while maintaining a sequence of targeted tidal volumes. The sequence of targeted tidal volumes, as described above, generally comprises delivering a large volume of the respiratory gas in the early tidal recruitment to shift the respiratory gas into the lung as the patient recruits and taper down the volume of the respiratory gas delivered as the recruitment progresses, thereby minimizing or preventing hyperventilation of the patient 102. This increases safety of recruitment maneuvers, while streamlining workflow for the clinician.

With continued reference to FIG. 1, in one embodiment, the regulation unit 108 of the ventilator 100 may include a processor (not shown) that is programmed to control the gas delivery unit 105, such that the gas delivery unit 105 delivers sequential breaths of respiratory gas having the predetermined tidal volume. The processor is in electrical communication with the gas delivery unit 105 and the plurality of sensors 118. A real time operating system is the foundation of the processor (not shown), which runs the algorithms required for measurement and control.

Accordingly, in another embodiment, a computer readable media comprising computer readable program instructions for ventilating the patient 102 is provided. The computer readable program instructions can be configured to automatically set the peak airway pressure and the tidal volume, and further be configured to make initial predictions for the PEEP using a compliance measurement as described above.

The computer readable program instructions comprise a routine for placing the ventilator 100 in a mode capable of delivering the respiratory gas based on at least one fixed parameter and at least one variable parameter; a routine for identifying a first level for the PEEP, a routine for configuring the ventilator 100 to deliver the respiratory gas at the peak airway pressure and the PEEP to achieve a set tidal volume, a routine for monitoring respiratory gas flow over time to measure tidal volume, a routine for setting a second level for the PEEP based on the measured tidal volume, a routine for automatically adjusting the PEEP to the second level, relative to the peak airway pressure and a routine for repeating the steps of configuring, monitoring, setting and automatically adjusting to achieve the ventilation.

As described in the methods 200 and 300, the PEEP is adjusted breath to breath relative to the peak airway pressure, to deliver a fixed tidal volume of the respiratory gas to the patient 102. When the airway pressure rises above a clinically indicated level of positive end-expiratory pressure (PEEP), the lung may be over pressurized, thus the effective airway pressure during the expiratory cycle may be titrated at least during a part of the expiratory phase under precise algorithmic control. The value of PEEP, during each breath, may be monitored by the ventilator 100 with the help of an alarm 120 coupled to the regulation unit 108. Accordingly, the invention further provides a method for monitoring the PEEP value.

In one embodiment, an absolute value of the PEEP may be monitored. The user may define a range for the acceptable values of the PEEP by identifying a first threshold value and a second threshold value. The first threshold value corresponds to a lowest acceptable value of the PEEP and the second threshold value corresponds to a highest acceptable value of the PEEP. The alarm 120 is configured to be triggered when the value of the PEEP exceeds the predetermined range defined by the first threshold value and the second threshold value.

In another embodiment, the user may set an absolute threshold value whereby the first threshold value and the second threshold value are selected such that the absolute value of the first threshold value and the absolute value of the second threshold value are equal to the absolute threshold value. The alarm 120 may be configured to be triggered when the PEEP exceeds the absolute threshold value.

In yet another embodiment, the PEEP may be monitored relative to a predetermined peak airway pressure. The user operating the ventilator 100 may define a range of acceptable PEEP values relative to the peak airway pressure. For this purpose, the difference between the PEEP value and the peak airway pressure may be determined. Further, a first relative threshold value and a second relative threshold value defining the range of acceptable PEEP values may be defined. The first relative threshold value corresponds to the lowest acceptable difference between the PEEP and the peak airway pressure and the second relative threshold value corresponds to the highest acceptable difference between the PEEP and the peak airway pressure. Accordingly, the alarm 120 may be configured to be triggered when the value of the PEEP falls outside the predetermined range by exceeding one of the first relative threshold value and the second relative threshold value.

Initially, the clinician enters the threshold values into the ventilator 100 by way of the user interface 110 coupled to the regulation unit 108. The current value of the PEEP is compared with at least one set of threshold values by the regulation unit 108. Upon determining that the value of the PEEP exceeds at least one of the first threshold value, second threshold value, first relative threshold value and the second relative threshold value, the alarm 120 coupled to the regulation unit 108 generates a signal, such that the gas delivery unit 105 changes the amount of PEEP produced by the ventilator 100. Alternatively, the user can directly adjust the peak airway pressure by manipulating a plurality of controls on the user interface 110 of the ventilator 100.

The system and method of ventilating a patient provided herein improve safety and patient outcome as a result of the ability to safely and reliably deliver optimal recruitment maneuvers.

The ventilator provided herein reduces interaction/workload demand on the clinician and allows less skilled users to successfully achieve lung recruitment.

In various embodiments, a ventilator for respiratory treatment of a patient is described. However, the embodiments are not limited and may be implemented in connection with different applications. The application of the invention can be extended to other areas, for example anesthetic devices. The design can be carried further and implemented in various forms and specifications.

This written description uses examples to describe the patient matter herein, including the best mode, and also to enable any person skilled in the art to make and use the patient matter. The patentable scope of the patient matter is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal language of the claims.

What is claimed is:

1. A method of ventilating a patient, the method performed by a ventilator, the method comprising:
   placing a ventilator in a mode capable of delivering respiratory gas based on at least two fixed parameters and at least one variable parameter, the fixed parameters including tidal volume and peak airway pressure and the variable parameter including positive end expiratory pressure (PEEP);
   identifying a first level for the PEEP;
   configuring the ventilator to deliver the respiratory gas at the peak airway pressure and the first level of PEEP to achieve the fixed tidal volume;
   monitoring respiratory gas flow over time to measure tidal volume;
   setting a second level for the PEEP based on the measured tidal volume;
   automatically adjusting through the ventilator, the PEEP to the second level, relative to the fixed peak airway pressure to keep the measured tidal volume at the fixed tidal volume; and
   repeating the steps of configuring, monitoring, setting and automatically adjusting to achieve the ventilation.

2. The method of claim 1, wherein the peak airway pressure is peak inspiratory pressure.

3. The method of claim 1, wherein the mode of ventilation is selected from the group consisting of pressure control, flow control, volume control and pressure regulated volume control mode of ventilation.

4. The method of claim 1, wherein the first level for the PEEP is identified based on airway impedance of the patient.

5. The method of claim 4, wherein the airway impedance of the patient is dependent on one or more mechanical properties of the lung including lung compliance.

6. The method of claim 1, wherein the fixed parameters further include oxygen content of the respiratory gas, respiratory rate and inspiration time.

7. A method of ventilating a lung in a patient, the method performed by a ventilator, the method comprising the steps of:
   determining a first peak airway pressure, which is fixed in relation to a first fixed tidal volume;
   selecting a first level for PEEP;
   providing respiratory gas to the patient at the first peak airway pressure and PEEP to deliver the first fixed tidal volume of the respiratory gas;
   varying the peak airway pressure to a second value, which is fixed in relation to a second fixed tidal volume;
   monitoring respiratory gas flow over time to measure a second measure tidal volume;
   determining a second level for the PEEP based on the second measured tidal volume;

automatically adjusting, through the ventilator, the second PEEP relative to the second fixed peak airway pressure to keep the second measured tidal volume at the second fixed tidal volume; and providing the respiratory gas to the patient at the second fixed peak airway pressure and the PEEP to deliver the second fixed tidal volume of the respiratory gas;

wherein each of the volumes of the respiratory gas being delivered is based upon a corresponding predetermined PEEP.

8. The method of claim 7, wherein varying the peak airway pressure comprises increasing the peak airway pressure and measuring the tidal volume comprises measuring expiratory tidal volume.

9. The method of claim 7, wherein varying the peak airway pressure comprises decreasing the peak airway pressure and measuring the tidal volume comprises measuring inspiratory tidal volume.

10. The method of claim 7, wherein measuring the tidal volume comprises measuring ventilation flow rates.

11. A computer readable media comprising non-transitory computer readable program instructions for ventilating a patient, the computer readable program instructions comprising:

a routine for placing a ventilator in a mode capable of delivering respiratory gas based on at least two fixed parameters and at least one variable parameter; the fixed parameters including tidal volume and peak airway pressure and the variable parameter including PEEP;

a routine for identifying a first level for the PEEP;

a routine for configuring the ventilator to deliver the respiratory gas at the first level of peak airway pressure and the PEEP to achieve the fixed tidal volume;

a routine for monitoring respiratory gas flow over time to measure tidal volume;

a routine for setting a second level for the PEEP based on the measured tidal volume;

a routine for automatically adjusting the PEEP to the second level, relative to the fixed peak airway pressure to keep the measured tidal volume at the fixed tidal volume; and a routine for repeating the steps of configuring, monitoring, setting and automatically adjusting to achieve the ventilation.

12. The computer readable media of claim 11, wherein the peak airway pressure is peak inspiratory pressure.

13. The computer readable media of claim 11, wherein the mode of ventilation is selected from the group consisting of pressure control, flow control, volume control and pressure regulated volume control mode of ventilation.

14. The computer readable media of claim 11, wherein the first level for the PEEP is identified based on airway impedance of the lung.

15. The computer readable media of claim 14, wherein the airway impedance of the lung is based on one or more mechanical properties of the lung including lung compliance.

16. The computer readable media of claim 11, wherein the fixed parameters further include oxygen content of the respiratory gas, respiratory rate and inspiration time.

\* \* \* \* \*